United States Patent [19]
Wendell et al.

[11] Patent Number: 5,147,336
[45] Date of Patent: Sep. 15, 1992

[54] ADAPTER KIT FOR A CATHETER INTRODUCER

[75] Inventors: Amy M. Wendell, Franklin; James P. Cianci, Walpole, both of Mass.

[73] Assignee: The Kendall Company, Mansfield, Mass.

[21] Appl. No.: 533,185

[22] Filed: Jun. 5, 1990

[51] Int. Cl.⁵ .............................................. A61M 25/00
[52] U.S. Cl. ...................................... 604/283; 128/673
[58] Field of Search ............................... 128/666-667, 128/672-675; 604/165, 167, 169, 256, 178, 283, 905, 246; 285/331, 338, 346, 356-357, 918; 206/364

[56] References Cited

U.S. PATENT DOCUMENTS

| | | | |
|---|---|---|---|
| 3,893,451 | 7/1975 | Durand et al. | 128/673 |
| 4,842,592 | 6/1989 | Caggiani | 604/283 |
| 4,856,529 | 9/1989 | Segal | 128/673 |
| 4,857,062 | 8/1989 | Russell | 604/167 |
| 4,895,346 | 1/1990 | Steigerwald | 604/167 |

FOREIGN PATENT DOCUMENTS 0360286  3/1990  European Pat. Off. ............ 128/675

OTHER PUBLICATIONS

A. Damenstein, R. L. Stout, H. U. Wessel, M. H. Paul "Electronic compensator for pressure waveform distortion by fluid-filled catheters" Medical & Biological Engineering vol. 14 No. 2 pp. 186-192 Mar. 1976.

*Primary Examiner*—C. Fred Rosenbaum
*Assistant Examiner*—Mark Bockelman
*Attorney, Agent, or Firm*—Alvin Isaacs

[57] ABSTRACT

An adapter kit 32 for a catheter introducer 31 wherein catheter 34 is passed into the body to transmit a medium through lumen 35 in catheter 34. Coupling means 95 is provided for compressing compression glands 48a and 48b against catheter 34 in a controlled manner in a catheter gripping position in FIG. 13, so that maximum resistance to catheter 34 pull-out is provided without distorting any medium transmitted by lumen 35. A related method is provided for sizing and using compression gland(s) 48.

11 Claims, 4 Drawing Sheets

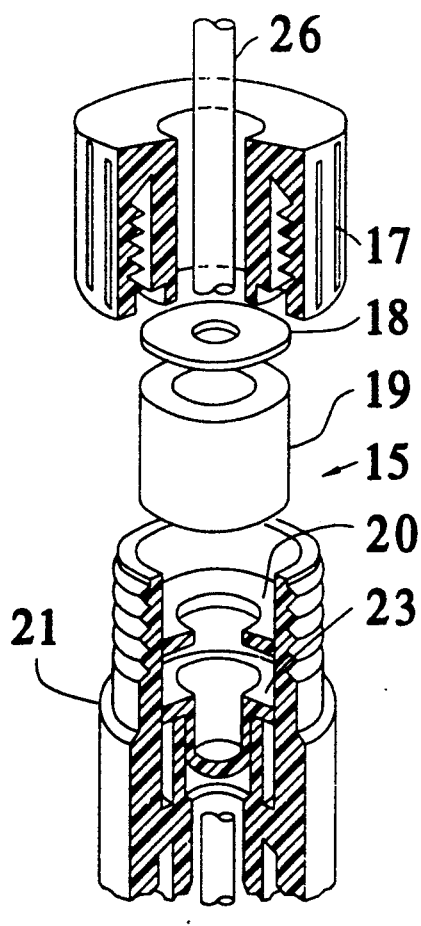
FIG. 1
PRIOR ART
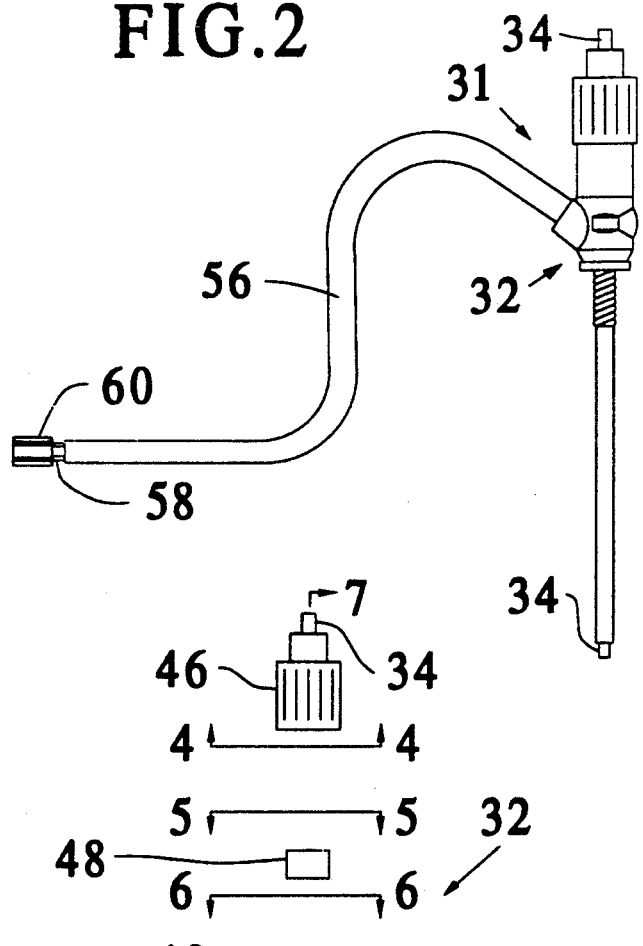
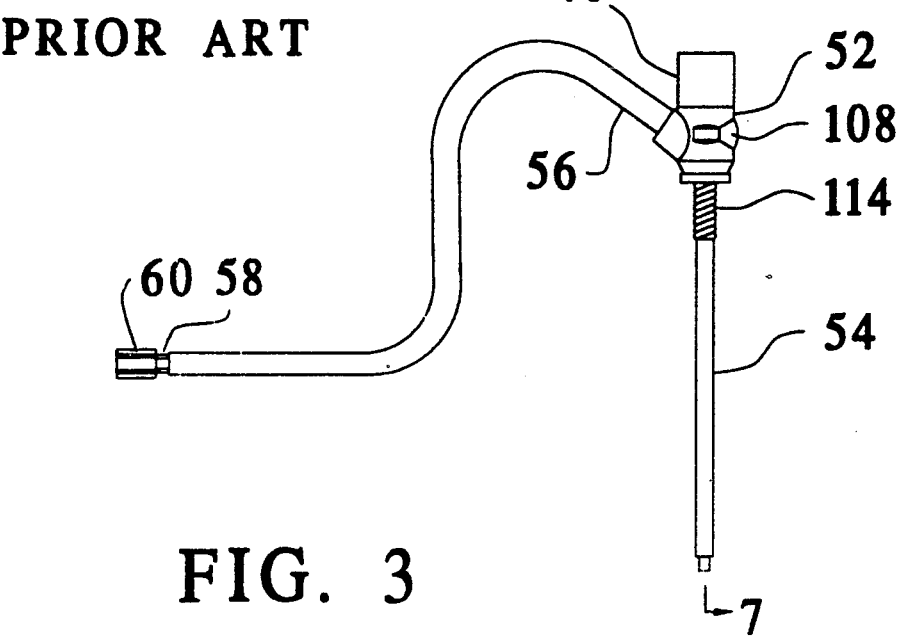
FIG. 3

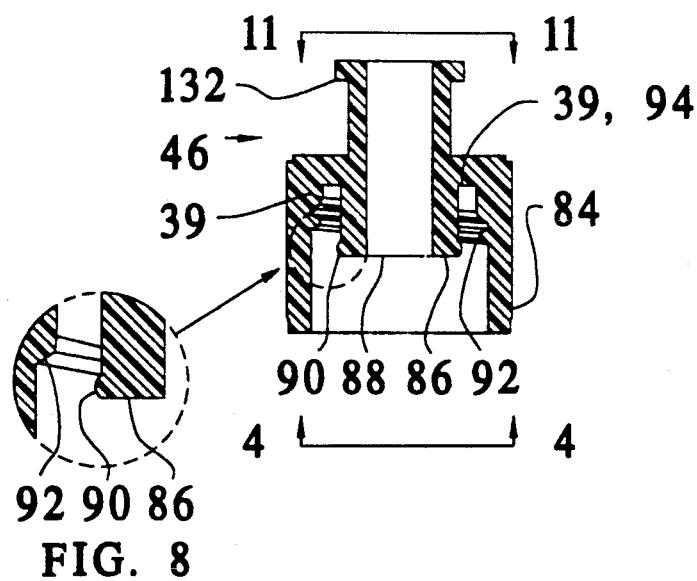
FIG. 8
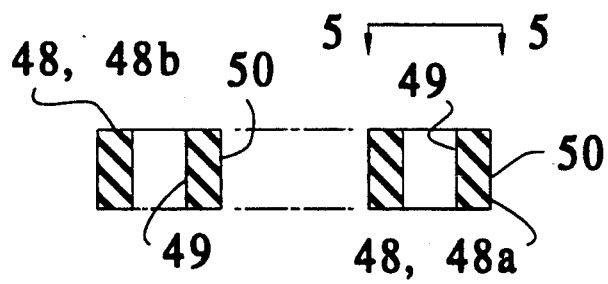
FIG. 9
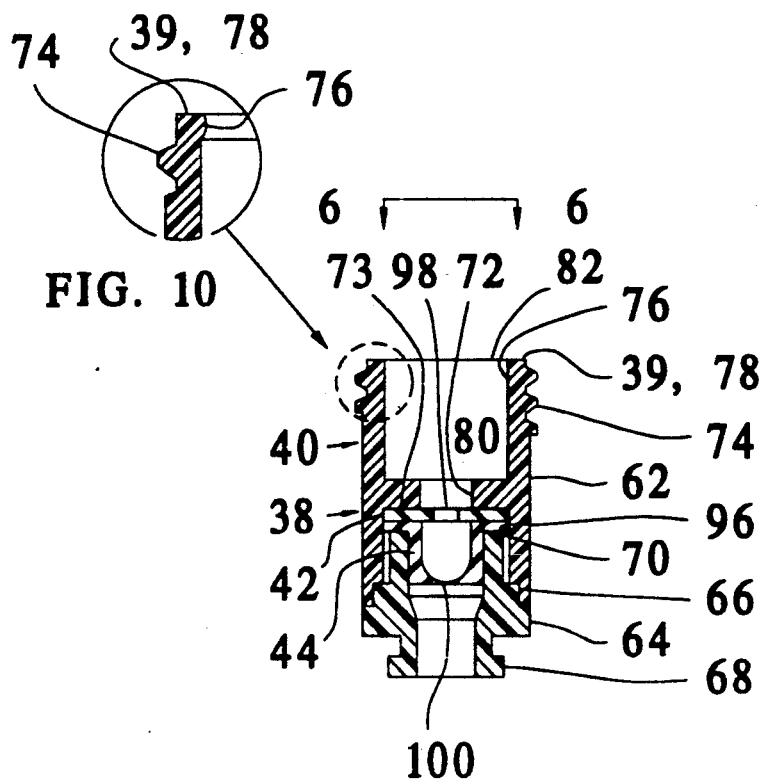
FIG. 10
FIG. 7

ADAPTER KIT FOR A CATHETER INTRODUCER

CROSS REFERENCE TO RELATED APPLICATION AND/OR PATENT

Related is: (1) U.S. Pat. No. 4,895,346 (hereinafter "U.S. Pat. No. '346"), patented Jan. 23, 1990 by inventor Carl J. Steigerwald and by common assignee The Kendall Company, and entitled VALVE ASSEMBLY; and (2) U.S. patent application Ser. No. 453,522, filed Dec. 20, 1989 now abandoned by inventor Carl J. Steigerwald and by common assignee The Kendall Company, and entitled VALVE ASSEMBLY, which is a division application of said U.S. Pat. No. '346.

BACKGROUND OF THE INVENTION

1. Field of the Invention

The field of the invention is to an adapter kit for a catheter introducer, and related method, wherein a catheter is passed into the body in order to transmit a medium either into or from the body through a lumen in the catheter. Of particular interest are heart catheters which are introduced into the heart for monitoring the heart by having its waveforms transmitted from the heart through a lumen in the catheter. The invention will accordingly be described in detail hereinafter by reference to heart catheters wherein the medium transmitted is the waveform for heart monitoring. Furthermore, the waveform distortion hereinafter referred to is the additional waveform distortion caused by the compressive forces used to grip the catheters within the body of the adapter. The waveforms transmitted by the catheters have other inherent distortions caused by resonance, air bubbles, etc. It is not the purpose of this invention to cure those inherent distortions. Additionally, the catheter must be of the type which can be compressed by application of compressive force and must contain a medium for transmitting a waveform which would make that waveform susceptible to compression of the catheter. Rigid catheters that break before deforming under compression or catheters which contain wires for transmitting waveforms are not susceptible to compression of the catheter and therefore will not greatly benefit from this invention.

2. Description of the Related Art

The problems involved in the prior art occur when the catheter contains a lumen for transmitting waveforms for monitoring a heart, which lumen can easily be crushed and/or have any of its transmitted waveforms distorted.

The related prior art has two types of potential problems: Type A problems, Type B problems, and Type C problems.

Type A problems are illustrated by: (1) the Prior Art Tuohy-Borst adapter in FIG. 1 of the Prior Art drawing in the present application; and (2) the related Steigerwald U.S. Pat. No. '346 mentioned first herein.

Type A problems are illustrated by Tuohy-Borst adapter 15 in FIG. 1 for a catheter introducer. It includes adjustable compression cap 17; latex washer 18 forming a seal around catheter 26 to prevent air leaks toward the patient and fluid leaks away from the patient; silicone compression sleeve 19 squeezing around catheter 26 when top cap 17 is tightened to hold catheter 26 in place; hemostasis valve 23 utilizing a duckbill, one-silt design to reduce the potential of air entry and blood loss when catheter 26 is not in place; and nylon washer 20 used to transmit an even force on valve 23, so that valve 23 is positioned correctly in body 21 housing hemostatic valve 23 and compression sleeve 19.

Tuohy-Borst adapter 15 is currently used to secure in place a pulmonary catheter having a lumen, after the catheter has been properly positioned. Problems occur because of the inability of its user to control automatically how much compression cap 17 is tightened, so that the lumen is not crushed or any of its transmitted waveforms distorted.

Adjustable cap 17 is tightened to secure its catheter 26 in place after catheter 26 has been properly axially positioned. However, if compression cap 17 is tightened too much, catheter 26 may become crushed and its transmitted waveforms distorted; but if cap 17 is not tightened enough, catheter 26 will not be properly secured in the position desired against movement relative to adapter 16.

Consider the uncontrolled tightening action: (1) by compression cap 17 on silicone sleeve 19 in adapter 15 in FIG. 1 of the Prior Art drawing in the present application; and (2) on elastic sleeve 112 in U.S. Pat. No. '346 (see lines 33-45, column 7). This uncontrolled tightening is likely to crush any lumen carried by catheter 26, and distort its transmitted waveforms.

Type B problems are illustrated by U.S. Pat. No. 4,000,739 (hereinafter called "U.S. Pat. No. '739"), patented Jan. 4, 1977 by Robert C. Stevens and entitled HEMOSTASIS CANNULA.

In Type B: U.S. Pat. No. '739 operates in a different manner than gland 48 in the present application, since cannula 10, 12 in U.S. Pat. No. '739: (1) relies on the support of gasket 22 to close slit 28 to resist the force exerted by the patient's blood pressure and prevents any blood loss (see lines 40-45, column 3); (2) does not have a mechanism for adjusting the compression, i.e., tightening down around its catheter 46 to immobilize it in place for preventing it from migrating from the desired fixed position; and (3) in its commercially sold form has its cap 12 and body portion 10 welded together, so its disc 22 or 24 cannot be replaced.

Type C problems are illustrated by U.S. Pat. No. 4,177,814 (hereinafter called "U.S. Pat. No. '814"), patented Dec. 11, 1979 by William R. Knepshield and entitled SELF-SEALING CANNULA.

In Type C: U.S. Pat. No. '814 has a trocar, which is a surgical instrument with a rigid metal shaft 18; and is not relevant to the catheter (and to its adapter, art and problems) disclosed in this application. When its rigid metal shaft 18 is removed, air entry and blood loss is prevented by automatically closing sealing slot 30 in valve 26 due to the compressive force (see lines 39-41, column 3). The force required to automatically close its central sealing slot 30 is likely to be sufficient force to crush any lumen carried by any catheter, and to distort its transmitted waveforms.

Adapter 32 of the present invention is an improvement on, and solves and eliminated the aforementioned defects and problems in, the prior art; takes the "guess work" out of the operation; and is designed: (1) to provide maximum resistance to any catheter 34 pull-out force, and (2) not to crush lumen 35 carried by catheter 34, or to distort any catheter monitoring wave forms transmitted by its lumen 35.

SUMMARY OF THE INVENTION

The invention relates to any adapter 32 for a catheter introducer 31 wherein catheter 34 is passed into the heart for monitoring the heart by having its waveforms transmitted from the heart through lumen 35 in catheter 34. Coupling means 95 is provided for compressing compression gland 48 against catheter 34 in a controlled manner in a catheter gripping position in FIG. 13, when compression member 46 is positively stopped by engagement of stop shoulders 78 and 94, so that maximum resistance to catheter 34 pull-out is provided without distorting any waveform transmitted by lumen 35. A related method is provided for sizing and using compression gland(s) 48.

One object of the invention is to provide an adapter kit for a catheter introducer, and related method, designed: (1) to provide maximum resistance to any catheter 34 pull-out force, and (2) not to distort any catheter monitoring waveform transmitted by its lumen 35.

A further object of the present invention is to provide for an adapter kit for a catheter introducer, a method for sizing and using interchangeable glands in the adapter.

A further object of the present invention is to provide an adapter kit for a catheter introducer, and related method, characterized by its ease of assembly of its component parts and ease of use of its method steps, structural and method simplicity, many desirable operating and use features, multiplicity of functional advantages for some of its component structural parts and method steps, attractive exterior appearance, and safe, reliable and precise operating characteristics.

These and other objects, novel features and additional advantages of the present invention will become more clearly apparent to one skilled in the pertinent art by reference to the appended claims as the following detailed description of the preferred embodiments(s) of the invention and discussion proceeds in conjunction with the accompanying drawing, wherein like elements are given like reference numerals throughout. The drawing is not necessarily to scale; emphasis instead is being placed upon illustrating the principles of the invention.

BRIEF DESCRIPTION OF THE DRAWING

In the drawings,

FIG. 1 is longitudinal, exploded view of a prior adapter for a catheter introducer;

FIG. 2 is a side elevational view of the catheter introducer with its component adapter of the present invention, and of portions of its associated catheter and sidearm;

FIG. 3 is a side elevational view of the catheter introducer of FIG. 2 with its component adapter shown in longitudinally exploded view;

FIG. 7 is an enlarged, longitudinally expanded or exploded, longitudinal, sectional view of component parts of the adapter taken generally along line 7—7 in FIG. 3 with the component parts in the disassembled position, which component parts are movable axially in a step-by-step action from the disassembled position in FIG. 7, through the "Free Spin" position (or intermediate position) in FIG. 12, to the assembled, and catheter gripping position in FIG. 13;

FIG. 8 is an enlarged, fragmentary, cross-sectional view (within the dashed line circles, as connected by the line and arrow) of a portion of the compression member in the upper portion of the adapter in FIG. 7;

FIG. 9 is a longitudinal, sectional view of an axially shorter compression gland interchangeable with the axially longer, corresponding compression gland shown in the mid-portion of FIG. 7;

FIG. 10 is an enlarged, fragmentary, cross-sectional view (within the dashed line circles, as connected by the line and arrow) of a portion of the body member in the lower portion of the adapter in FIG. 7;

DESCRIPTION OF THE PREFERRED EMBODIMENT(S)

FIGS. 2-14 disclose catheter introducer 31, and its component adapter 32, of the present invention for catheter 34 having at least one lumen 35.

Figure 13:
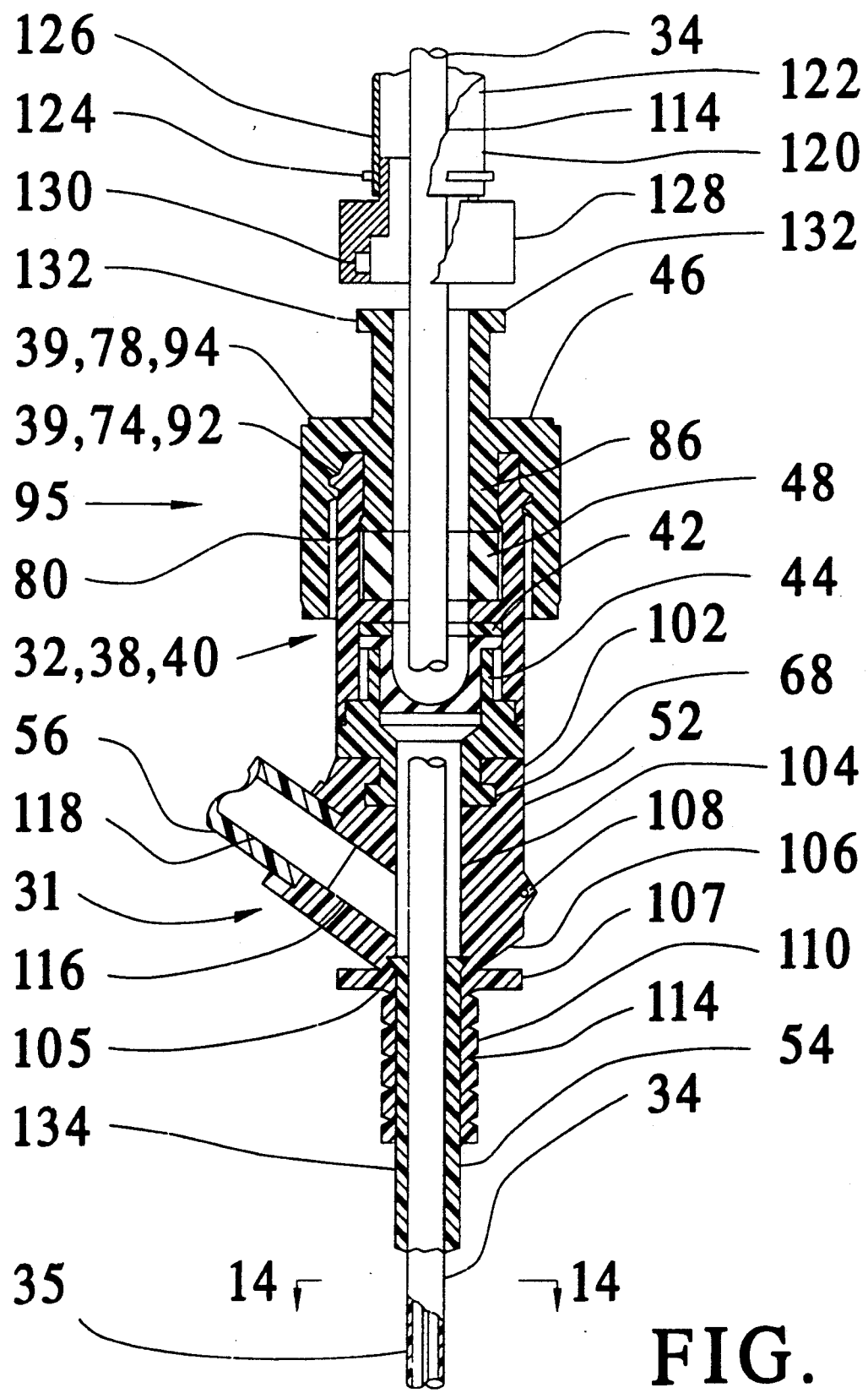
FIG. 13 is a longitudinal, sectional view taken generally along line 13—13 in FIG. 11, and taken in the plane of the drawing in FIG. 2, of the catheter introducer, and its adapter, with its component parts in the assembled, and catheter gripping, position.

In FIG. 7, adapter 32 comprises the following three mating parts, which have been shown assembled in FIGS. 2 and 13:

(1) hemostasis valve assembly 38 in the lower part of FIG. 7, including body member 40, sealing washer 42 and duckbill valve 44;

(2) compression member 46 in the upper part of FIG. 7; and (3) compression gland 48 in the central part of FIG. 7.

Introducer 31 in FIGS. 2, 3 and 13 comprises not only aforementioned adapter 32 but also: (1) transition member 52 with sheath 54; and (2) side arm 56, female luer adapter 58, and male luer cap 60.

Body member 40 (sometimes called hemovalve body or hemovalve body member 40) in FIGS. 7 and 10 includes separate upper body member element 62 and lower body member element 64 to facilitate assembly of body member 40. After assembly, the two, spaced apart, separate body member elements 62, 64 are welded and secured together all around by circumferential, sonic weld 66. Body member 40: (1) has in its lower element 64, annular shoulders 68 and 70; and (2) has in its upper element 62: (a) annular flange 72 in its lower portion; and (b) in its upper portion, external threads 74, annular bore lip 76, stop shoulder 78, and internal cavity 80 having opening 82, so body member 40 is sometimes called a hollow member.

Figure 12:
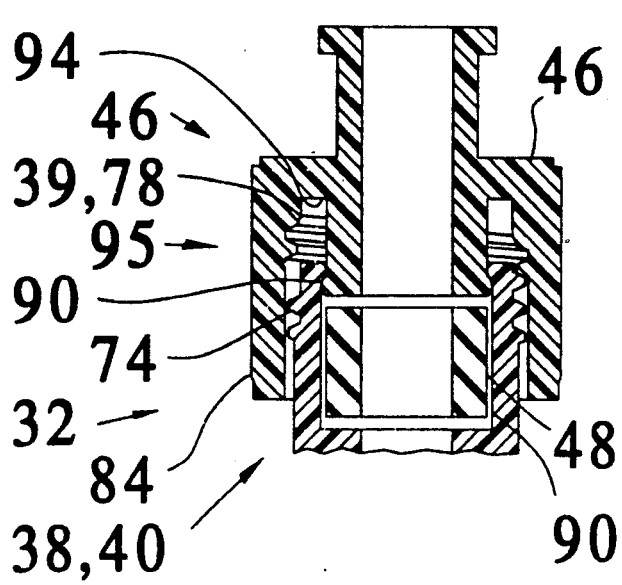
FIG. 12 is a longitudinal, sectional view taken generally along line 12—12 in FIG. 11 of the adapter for a catheter introducer with its component parts in the "Free Spin" position, or intermediate position.

During assembly of body member 40 and compression member 46, these members sequentially move axially toward each other from the expanded, disassembled position in FIG. 7, through the intermediate position in FIG. 12, into the assembled, or catheter gripping, position in FIG. 13.

During this assembly, compression member 46 (sometimes called cap, compression nut, or cap member 46) in the upper part of FIG. 7 has: (1) its external annular rim or sleeve 84 over threads 74 and over outer surface of body member 40; (2) its internal annular flange or tubular plunger 86 having port 88, encircling catheter 34, being aligned with cavity 80 of body member 40 for a purpose to be described in more detail hereinafter, and having its annular outer lip 90 snapping with a detent type action axially past annular bore lip 76 of body member 40 into the FIG. 12 position; and (3) its internal threads 92 engaging with external threads 74 on body member 40 in order to adjust compression member 46 relative to body member 40 from the FIG. 12 position into the FIG. 13 position, determined by its stop shoulder 94 engaging against stop shoulder 78 on body member 40.

Body member 40 in the lower part of FIG. 7 has: (1) a hemostasis valve, here elastic duckbill valve 44, in communication with cavity 80 and having its outer annular flange 96 resting on annular shoulder 70 of body member 40; (2) sealing washer 42, preferably a latex washer, located in flow communication with cavity 80 and against valve 44, and having its central opening 98: located intermediate valve 44 and annular flange 72, receiving catheter 34, and sealing against the outer surface of catheter 34, since opening 98 is smaller than the outside diameter of catheter 34; and (3) shelves or annular flanges 70 and 72, and two annular projections 73 on the bottom of flange 72 (each triangular in cross section) for engaging washer 42, for retaining valve 44 and washer 42 in place between body elements 62 and 64. Duckbill valve 44 has single slit 100: (1) adjacent the lower, distal, end of cavity 80 in FIG. 7 in fluid communication with cavity 80; (2) permitting passage of catheter 34 therethrough and sealing against the outer surface of catheter 34; and (3) if catheter 34 has been removed, preventing passage of blood or air through closed valve 44.

In FIGS. 7, 9 and 13, elastic, cylindrical, compression gland 48, an elastomeric means or gland, operates in conjunction with, and between, body member 40 and compression member 46; is located in cavity 80; rests on top of annular flange 72, serving as a floor for gland 48; and may be made of any suitable elastic material, such as silicone, natural rubber or a thermoplastic elastomer, but has been made herein as a silicone elastomeric gland 48 with a 40 shore A (durometer hardness). Two different sized glands 48 are shown in FIGS. 7 and 9 as glands 48a and 48b, each usable in adapter 32; but with only gland 48a shown as aligned for assembly in FIG. 7.

In use, catheter 34 passes through bore 49 of gland 48, opening 98 of washer 42, and slit 100 of valve 44, with washer 42 sealing against the outer surface of catheter 34.

Transition member 52 in FIG. 13 has: (1) its upper end 102 fixedly secured at annular shoulder 68 to the lower end of body member 40; (2) flow passageway 104 extending therethrough; (3) elongated sheath 54 fixedly secured in its lower end by tapered portion 105 at its upper end; (4) suture eye 108 for detachably securing introducer 31 to the patient; and (5) downwardly extending in FIG. 13 tapered portion 106, flange 107, and lower distal portion 110, having helical grove 114 in its outer surface surrounding sheath 54, to provide strain relief for sheath 54 and to reduce the possibility of kinking of sheath 54 during use, and especially if bending occurs when there is no catheter extending through sheath 54.

Introducer 31 in FIGS. 2, 3 and 13 has elongated sidearm or conduit 56 secured to side port 116 of transition member 52 with its lumen 118: (1) at one end being in fluid communication with bore 104 of transition member 52, and (2) at its other end with any desirable components, such as female luer adapter 58 having opposite ends telescoped into male luer cap 60 and lumen 118.

In the upper part of FIG. 13, covering member 120 for catheter 34 has elongated, flexible sleeve 122 attached by O-ring 124 to annular flange 126 of connection member 128. Connection member 128 has internal threads 130 screwing onto thread segments 132 on compression member 46 in FIG. 11 for releasably locking connection member 128 onto the upper end of compression member 46 for preventing sleeve 122 from being inadvertently removed from compression member 46.

Using introducer 31 involves these steps. First, an intravenous catheter and needle assembly, with the needle located inside the catheter, is inserted into a suitable vein, usually located in the patient's neck area and going directly to the heart, such as the internal or external jugular vein, subclavin vein, etc. After insertion into the vein, the needle is removed from the catheter. Next, a guide wire is inserted through the catheter until it is located in the vein, and the catheter is removed over the guide wire. Next, a dilator, having a channel extending therethrough, is passed through introducer 31; into its sheath 54; and over the guide wire until sheath 54 is located in the vein. At this time, the dilator and guide wire are removed from introducer 31, with sheath 54 in place in the vein. Sidearm 56 and sheath 54 may be flushed, either at this time or before placing sheath 54 in the vein.

Catheter 34 may be passed through introducer 31 and sheath 54, either before or after attachment of covering member 120 to compression member 46. Inserted catheter 34 extends through compression member 46, bore 49 of gland 48, body member 40 and sheath 54 into the vein. After covering member 120 is telescoped over catheter 34 and is locked in place, flexible sleeve 122 extends over, and protects, catheter 34 during use of introducer 31.

Catheter introducer 31 and catheter 34 may be of may different types, but here are preferred types for this usage. Introducer 31 is a percutaneous catheter introducer, here a pulmonary catheter introducer. Catheter 34, here a pulmonary arterial catheter 34 (for example, a PAC catheter, or a Swan-Ganz catheter) is passed through introducer 31.

Catheter 34 may be used to infuse drugs into the venous system during use of introducer 31. Drugs may be infused from luer fitting 58 in FIG. 2 through lumen 118 in FIG. 13 of sidearm 56, channel 104, slight clearance 134 between the outside of catheter 34 and the bore of sheath 54, past catheter 34, and through sheath 54 into the patient's vein in order to feed a solution, such as heparin, into the vein to prevent blood clotting.

In FIG. 13, catheter 34 passes through central opening 98 in washer 42 and through duckbill type, hemostasis valve 44, where washer 42 seals against catheter 34 for preventing passage of air into sheath 54, and preventing passage of blood out through valve 44. With catheter 34 in place in introducer 31, compression member 46 may be adjusted relative to body member 40 (by having threads 74, 92 moving members 40, 46 axially closer together from the FIG. 12 to FIG. 13 positions upon relative rotation of members 40, 46) for applying pressure by internal tubular plunger 86 against gland 48 to bulge bore 49 of gland 48 inwardly for immobilizing and holding catheters 34 in place in introducer 31, as shown in FIG. 13.

Now, as to the mode of operation, introducer 31 has been inserted into the patient; and catheter 34 has been inserted into introducer 31, and slid through the vein, usually into the right atrium or right ventricle of the heart. Then, a balloon on catheter 34 is blown up, after it has been put into the pulmonary artery of the patient. The balloon wedges into the pulmonary artery; occludes the blood flow from the right side to the left side of the heart; and during this seclusion, allows medical personnel to monitor the heart, such as getting a feeling for what the left side of the heart is doing, such as measuring the pressures in the left side of the heart through lumen 35 in FIGS. 13 and 14.

Figure 5:
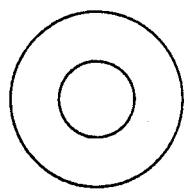
FIG. 5 is a transverse, sectional view taken generally along line 5—5 in FIG. 3.
Figure 4:
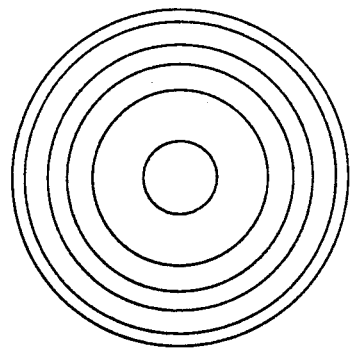
FIG. 4 is a transverse, sectional view taken generally along line 4—4 in FIG. 3.
Figure 11:
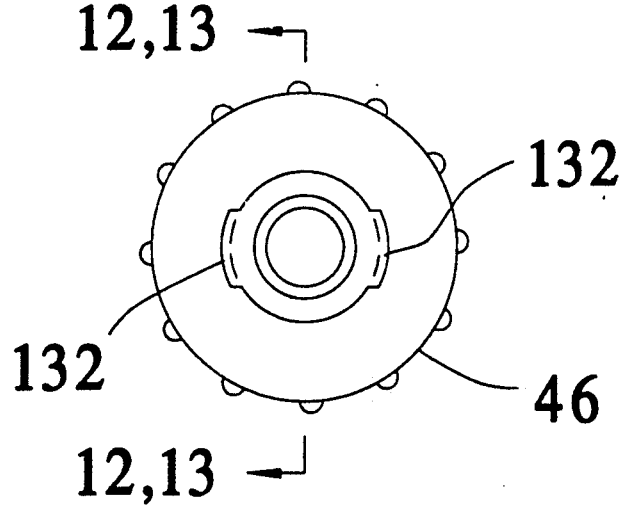
FIG. 11 is a top, plan view of the adapter for a catheter introducer in FIG. 7, and especially of its compression member in the upper portion of the adapter in FIG. 7.
Figure 6:
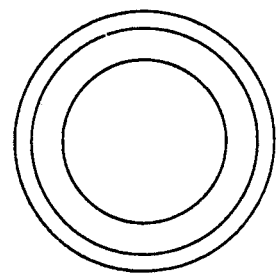
FIG. 6 is a transverse, sectional view taken generally along line 6—6 in FIG. 3.
Figure 14:
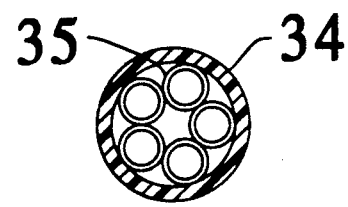
FIG. 14 is a transverse, sectional view taken generally along line 14—14 in FIG. 13 of the catheter showing a lumen therein for transmitting waveforms.

Although five lumens are shown in catheter 34 in FIG. 14, and could be used and discussed, only one lumen 35 is described herein for purposes of illustration and explanation. The hydraulic pressure through lumen 35 from the heart can be measured by a transducer, located outside the patient, to monitor the heart waveforms. Catheter 34 may contain additional lumens, as shown in FIG. 14, for other purposes. For example, some of these lumens may be used for blowing up the aforementioned balloon on catheter 34. Also, some of these other lumens may be used for a purpose wherein overly compressing the lumen prevents it from functioning properly, so the advantages of coupling 35 may also be used for it. The description hereafter herein will be restricted to only one lumen 35.

When catheter 34 is sitting in the heart, it is used to monitor the waveforms for the heart. Different conditions of different heart portions have different waveforms. Squeezing catheters 34 can distort: (1) lumen 35, (2) the waveforms received from the heart and transmitted through lumen 35, and (3) the medical data received and to be relied upon for diagnosis and treatment.

Adapter 32 for catheter introducer 31 includes coupling means 95 for carefully handling catheter 34 when catheter 34 has at least one lumen 35 in FIG. 14 for transmitting any waveform from the heart. Coupling means 95 [responsive to bringing together (by relative approach movement) members 40 and 46, and connecting members 40 and 46 together] compresses compression gland 48, and closes its gland bore 49, inwardly against catheter 34 by plunger 86 in a controlled manner in the catheter gripping position in FIG. 13 by the relative approach movement of tubular plunger 86 into cavity 80, so that: (1) maximum resistance to catheter 34 pull-out is provided without distorting any waveform transmitted by lumen 35, and (2) neither catheter 34 nor any lumen 35 is adversely crushed. Coupling means 95 includes: (1) adjusting means for adjusting the relative position of the members into said gripping position, comprising cooperating threads 74, 92 respectively on body member 40 and compression member 46; and (2) abutting stops 39 in FIGS. 7 and 13 on members 40, 46 determining said gripping position, with abutting stops 39 including engaging or abutting: (a) stop shoulders 78, 94 respectively on members 40, 46 determining said gripping position, and (b) threads 74, 92 ending in thread run out determining said gripping position. These abutting stops 39 not only determine said gripping position but also coact together to provide a double positive stop.

As to threads 74 and 92 ending in thread run out, thread run out is defined as one or both threads coming to an end, so that members 40 and 46 will be abruptly stopped thereby and cannot be screwed, relatively rotated, or axially advanced any farther in the thread advancing direction.

Once catheter 34 has been placed into the patient, it needs to be stabilized, so it doesn't become pulled out. This is done by tightening down on compression nut member 46 of adapter 32 until stop shoulders 78, 94 engage or abut, as shown in FIG. 13. Engaging stop shoulders 78, 94 insure not only that maximum resistance prevents catheter 34 being pulled out of the patient but also that catheter 34 is not crushed to adversely affect measurement through its lumen 35 of the pressures for the left side of the heart.

Catheter 34 is able not only to be passed into the heart into a monitoring position for heart monitoring purposes but also to be pulled out of the heart into a retracted position, such as at a time when heart monitoring is not required or desired. When catheter 34 is to be repositioned, compression member 46 is unscrewed by threads 74 and 92; bore 49 of gland 48 loosens its hold on catheter 34, so that gland 48 and sealing washer 42, located inside adapter 32, then allow axial movement of catheter 34 inside body member 40 into the retracted position without letting air enter or blood escape out; catheter 34 is repositioned axially in body member 40; and compression member 46 is tightened until stop shoulders 78, 94 reengage, so as to hold catheter 34 in the retracted position. After monitoring the heart is finished, the balloon is deflated. Thereafter, the deflated balloon and catheter 34 are pulled back from this monitoring or active position into this retracted or inactive position.

Now, passage of blood or air through valve 44 is still prevented, because sealing washer 42 opening 98 seals against the outer surface of catheter 34.

Catheter 34 may be removed from adapter 32 by following the catheter repositioning steps given above. If catheter 34 has been removed, passage of blood or air is prevented by the automatic closing of valve 44 after catheter 34 was removed.

Here is one suitable method of manufacturing introducer 31. Compression member 46 is formed of a rigid material, such as nylon. Body member 40 and preformed sheath 54 (each formed of a suitable material, such as urethane) are placed in a spaced relationship in a mold. Next, transition member 52 is injection molded in the mold from a suitable material, such as urethane, in order to form an integral, sealed construction of sheath 54 and body member 40, as shown in FIGS. 3 and 13, such that body member 40, transition member 52 and sheath 54 are integrally formed into one piece in a manner preventing leakage of air or blood through the bonds of the various component pieces, and are interlocked against separation by shoulder 68 on body member 40 and tapered portion 105 on the upper end of sheath 54.

Compression gland 48 is precisely dimensioned, and its sizing and use are carefully controlled.

Here is a method used for sizing gland 48, while gland 48 is located in cavity 80 and compressed against catheter 34 by compression member 46 moved toward gland 48. This method includes the steps of: (1) inserting gland 48 into cavity 80; (2) moving compression member 46 toward cavity 80, gland 48 and body member 40 to the catheter 34 gripping and member stopping position in FIG. 13 with stop shoulders 78, 94 engaged; (3) measuring the compressive force on catheter 34; and (4) correcting the size of gland 48, so that a preselected compressive force is not exceeded.

In the above method, the measuring of the compressive force may take either of these two different methods: (1) if the catheter 34 has at least one lumen 35 which is transmitting a waveform responsive to the compressive force applied by the gland 48, then the measurement involves measuring the amount the transmitted waveform is distorted by the compressive force; the size of the gland may then be selected so that a perselected amount of distortion is not exceeded; or (2) the measurement of the compressive force involves measuring the pull out force on the catheter 34 so that the compressive force is sufficient to prevent catheter pull out but not large enough to distort the waveform transmitted by lumen 35. Since the object of the invention is to eliminate, or at least minimize, the amount of distortion caused by the compressive force of the gland, the measurement of the amount of distortion of the waveform transmitted by lumen 35 in (1is the preferred method.

Incorporating the preferred method of measurement into the above sizing method, the preferred sizing method includes the steps of: (1) inserting the gland 48 into cavity 80; (2) moving compression member 40 toward cavity 80 into the catheter gripping position; (3) measuring the amount of distortion of the waveform transmitted by lumen 35; and (4) correcting the size of the gland 48, so that a preselected compressive force is not exceeded thereby eliminating, or at least minimizing, the amount of distortion.

If two, different sized, interchangeable glands 48, shown in FIGS. 7 and 9 as glands 48a and 48b respectively, were sized and used for corresponding catheters 34 having at least two different sized outside dimensions, the sizing and use of glands 48 would involve further the method steps of: (1) separately sizing these two different sized glands 48a and 48b, each by one of the methods in the preceding paragraph for its corresponding catheter 34; and (2) for the different sized catheters 34, interchanging glands 48a and 48b being used with the corresponding sized catheter 34.

Each compression gland 48 is precisely dimensioned to ensure that when compression member 46 is positively stopped by engagement of stop shoulders 78 and 94, the maximum resistance to catheter 34 pull-out in the catheter gripping position is achieved without distortion of any waveform transmitted by lumen 35 in catheter 34.

Consider this method by a different approach. Then, the volume for compressing any gland 48 in the catheter gripping position in FIG. 13 is a function of the location of stop shoulders 78, 94; the inside dimensions of cavity 80 (as bounded by flanges 72 and 86), and the following volumetric ration defined by the ratio of:

---
the volume of the compressed gland 48
in the catheter gripping position in FIG. 13
to
the volume around catheter 34 in its
surrounding cavity 80 (bounded by annular
flanges 72 and 86, and determined by engaged
stop shoulders 78 and 94) in the catheter
---

-continued
---
gripping position
--- defines a volumetric ratio, providing maximum resistance to catheter pull-out without adversely crushing catheter 34 or distorting any waveform transmitted by lumen 35 in catheter 34. For two, different sized, interchangeable glands 48a and 48b usable with catheters 34 having at least two different sized outside dimensions, the volumetric ration for a compressed gland in the catheter gripping position being substantially the same for both glands 48a and 48b as long as the following factors remain constant, and do not vary or change: (1) lumen 35, or any other effected lumen(s), in catheter 34, and (2) the characteristics of the gland material, such as its durometer hardness.

Here are some examples. Since different size (in outside diameter) catheter(s) may be used in an adapter, such as adapter 32, different size compression glands 48, such as gland 48a and 48b in FIGS. 7 and 9 respectively, are used interchangeably in cavity 80 of body member 40. Four different sized catheters 34 are commonly used, i.e., catheters Nos. 7.5, 7, 6 and 5 French respectively having outside diameters approximately 0.099, 0.092, 0.079 and 0.066 inch and using sheaths 8½, 8, 7 and 6 French. There is an advantage in having each gland 48 use the same inside diameter bore 49 and outside diameter periphery 50; and being cylindrical, or annular, with the same cross sectional shape in FIGS. 7 and 9, since glands 48 can then be made by an extrusion process and can be easily cut into different lengths from the same extrusion. Two annular, elastomeric, compression glands 48a and 48b, having the same outside diameters and inside diameters (each having bore 49 of approximately the same cross sectional dimension telescoped over its catheter 34), may be used for all four sizes of catheters 34 if each compression gland 48 is formed, or cut, in two different axial lengths, such as axially shorter gland 48b in FIG. 9 for the two larger outside diameter catheters, and axially longer gland 48a in FIG. 7 for the two smaller outside diameter catheters. The proper length of each gland 48 has been determined experimentally by some of the aforementioned methods, and this experiment: inserting a gland 48 (over catheter 34 of desired outside diameter size) into cavity 80 of body member 40, moving members 40 and 46 to the FIG. 13 assembled, or catheter gripping, position with engaged abutting stops 39 (including stop shoulders 78 and 94 fully engaged and threads 74, 92 ending in thread run out), and measuring the distortion of the waveforms transmitted by lumen 35. Repeating this experiment with different (outside diameter) sized catheters 34 and different length glands 48, measuring the distortion of the waveforms transmitted by lumen 35, and graphing the results will reveal the proper length glands 48 to use for each size catheter 34. Wave distortion should be reduced by cutting down the length of its gland 48. If each cylindrical compression gland 48 has an inside diameter of approximately 0.127 inch and an outside diameter of 0.285 inch, the shorter gland should be approximately 0.179 inch long and the longer gland should be approximately 0.191 inch long when the inside diameter of cavity 80 is approximately 0.299 inch for handling the four different sized catheters mentioned above.

The mode of operation is further described hereafter in detail. Numerous advantages are disclosed hereafter by slowly and carefully considering: (1) the step-by-step action of moving the component parts from the disassembled position in FIG. 7, through the "Free Spin" position in FIG. 12, to the assembled (or catheter gripping) position in FIG. 13; and (2) the structure and coaction of the component parts, and the use advantages obtained:

STEP NO. 1; PUSHING GLAND 48a OR 48b RESPECTIVELY IN FIG. 7 OR FIG. 9 AXIALLY INTO OPENING 82, PAST ANNULAR BORE LIP 76, AND INTO CAVITY 80 OF BODY MEMBER 40: The same snap past, or detent, action is provided for detachably holding any gland in cavity 80 by bore lip 76, because each elastomeric gland has an outside diameter dimension of its periphery 50 greater than the internal diameter dimension of bore lip 76 and fitting into the internal diameter dimension of cavity 80, so that gland 48 can be pushed and telescoped through mouth 82 into cavity 80 and detachably held in cavity 80 by bore lip 76, unless a significant axial, separating, pulling apart or disassembling force is exerted.

If different sized glands 48 are to be used interchangeably (as described in the preceding paragraph for different sized catheters and as illustrated in FIGS. 7 and 9), each of the different sized glands 48 will be detachably held in the same manner in cavity 80 by bore lib 76. Then, two elastomeric glands 48, each gland 48a and 48b of a different length, has approximately the same outside diameter dimension for fitting interchangeably in cavity 80 and for being held by same bore lip 76, so that gland 48a and 48b can be used interchangeably, each with a different outside dimensioned catheter 34 gripped by the compression of a different length gland 48.

STEP NO. 2; ANNULAR SLEEVE 84 ON COMPRESSION MEMBER 46 KEEPS THE PARTS COAXIALLY ALIGNED: Annular sleeve 84 of compression member 46 is coaxial with, and closely surrounds the periphery of, body member 40 and its threads 74, so helps keep members 40 and 46 coaxially aligned, and easily rotatable:

(1) in all positions, between and including FIGS. 7, 12 and 13 positions, and (2) in step Nos. 3, 4 and 5 described hereinafter, since this coaxial alignment prevents cocking, binding and misalignment of members 40 and 46, etc. The bore of sleeve portion 84 on one member 46 coaxially extends in close transverse alignment with, and surrounding, portions of a cylindrical surface on other member 40 (with these portions of a cylindrical surface being formed by crests of external threads 74 on other member 40 before engagement of threads 74, 92) for guiding members 40, 46 into coaxial alignment: (1) with threads 74, 92 aligned for engagement; (2) with no cocking of the component parts; and (3) for promoting free spin and rotational actions, as well as axial pushing, pulling and movement actions.

STEP NO. 3; PUSHING ANNULAR OUTER LIP 90 ON COMPRESSION MEMBER 46 AXIALLY INTO OPENING 82, PAST ANNULAR BORE LIP 76, AND INTO CAVITY 80 OF BODY MEMBER 40 INTO THE FIG. 12 POSITION "SNAPS" MEMBERS 40, 46 TOGETHER: Body member 40 has its cavity 80, and its mouth 82, aligned with, and to receive, tubular plunger 86 on compression member 46. Bore lip 76 at mouth 82 has an internal diameter dimensions less than the internal diameter dimension of cavity 80, and of outer lip 90 on the periphery of tubular plunger 86 on its end closest to cavity 80. As outer lip 90 moves axially past bore lip 76 into cavity 80, members 40 and 46 are detachably connected together by a "snap action".

During packaging, shipping and use of adapter 32, engaged annular lips 76, 90 help: (a) retain the component parts in properly assembled relationship, b) prevent disassembly and loss of component parts, and (c) maintain sterilization of some component parts and surfaces, especially those within adapter 32 close to catheter 34. The component parts will disassemble only if a substantial axial, separating force is exerted to pull apart members 40, 46 and annular lips 76, 90 by a "snap action".

STEP NO. 4; RELATIVELY ROTATING COMPRESSION MEMBER 46 ON BODY MEMBER 40 BY A "FREE SPIN" ACTION IN THE FIG. 12 POSITION: Each of lips 76 and 90, and cavity 80, are coaxial and annular in shape, so that members 40, 46 have a free spin, coaxial, rotational action without cocking or binding the component parts, even though the members are only detachably connected.

During packaging, shipping and use of adapter 32, accidental or unauthorized disassembly of adapter 32 is resisted in the FIG. 12 position, since this FIG. 12 position provides a "free-spin" relative rotational action between members 40 and 46; since neither threads 74, 92 nor stop shoulders 78, 94 are engaged; and since annular sleeve 84 of compression member 46 is coaxial with, and closely surround the periphery of, body member 40 and its threads 74 to help keep members 40 and 46 coaxially aligned during this "free-spin" action.

Since this free spin, coaxial, rotational action occurs before engagement of threads 74 and 92, this action guides members 40 and 46 into coaxial alignment with the threads aligned for engagement thereafter in the next step No. 5, and without cocking or binding of the component parts.

STEP NO. 5; AXIALLY PUSHING TOGETHER MEMBERS 40 AND 46 TOWARD EACH OTHER, AND RELATIVELY ROTATING MEMBERS 40 AND 46 IN THE THREAD ADVANCING DIRECTION: (A) UNTIL THREADS 74 AND 92 ENGAGE ON RESPECTIVE MEMBERS 40 AND 46, AND (B) ADVANCING MEMBERS 40 AND 46 TOWARD EACH OTHER (TOWARD THE FIG. 13 POSITION) BY THE THREAD ADVANCING ACTION OF COMPATIBLE THREADS 74 AND 92: Although threads 74 and 92, and stop shoulders 78 and 94 may take any suitable form or location, each of the threads 74 and 92 herein uses a ¾ turn, 20 pitch, single lead threads 74, 92 ending in thread run out as, and when, stop shoulders 78 and 94 engage or abut providing not only four abutting stops 39 but also a double positive stop determining catheter 34 gripping position. This ¾ thread turn makes for a very fast movement from FIG. 12 to FIG. 13 positions, requiring only a ¾ relative turn by members 40 and 46, and having a ¾ pitch axial thread length of about 0.0375 inch (¾ × 1/29).

STEP NO. 6; ENGAGING STOP SHOULDERS 78 AND 94 ON RESPECTIVE MEMBER 40 AND 46: Gland 48 is compressed inwardly to grip, and hold, catheter 34 by its gland bore 49 in the FIG. 13 position, after which stop shoulders 78 and 94 engage to stop further rotation of members 40 and 46 and further compression of gland 48, so as to prevent adversely crushing catheter 34, and its lumen 35.

When the FIG. 13 position is reached as stop shoulders 78 and 94 abut, a jamming, or lock-up, action occurs to lock members 40, 46 more firmly together in the FIG. 13 position then would have been otherwise expected, since threads 74, 92 end in thread run out as stop shoulders 78, 94 engage, and threads 74, 92 jam and lock up for securing members 40, 46 together in the catheter 34 gripping position in FIG. 13. This action is similar to a lock washer action on a tightened screw and nut. It provides the advantages of the lock washer without the disadvantages of a separate lock washed part, which would have surface difficult to keep clean.

All of the advantages described herein, and in these Steps No. 1-6 inclusive, are obtained efficiently with minimum effort and movement, because: (1) only a minimum compression of gland 48 is required since the outside diameter of gland 48 is only slightly smaller than the diameter of the bore of cavity 80 behind its bore lip 76; (2) only a minimum difference exists between the internal, diametrical dimensions of bore lip 6 and cavity 80, so that only minimum relative approach movement of members 40, 46 is required for compressing gland 48 and for movement into the catheter gripping position; and (3) since only minimum relative approach movement of member 40, 46 is required, each of the threads 74 and 92 need not be substantially more than a 3/4 pitch axial thread length.

It should now be apparent that: (1) Adapter 32 is easy to use, in view of its many features described herein; (2) Each compression gland 48 is precisely dimensioned to ensure that when compression member 46 is positively stopped by engagement of stop shoulders 78 and 94, the maximum resistance to catheter 34 pull out in the catheter gripping position is achieved without distortion of any wave form transmitted by lumen 35 in catheter 34; (3) Glands 48 are interchangeable, and are easily made by cutting an extrusion into proper length(s); and (4) Using adapter 32 eliminates the problems encountered in the prior art, and takes the "guess work" out of this operation of providing maximum resistance to catheter 34 pull-out in the catheter gripping position without distortion of any waveform transmitted by lumen 35 in catheter 34.

This invention may be embodied in other specific forms without departing from the spirit or essential characteristics thereof. It is understood that: the present embodiment(s) are therefore to be considered in all respect as illustrative and to restrictive, the words which have been used are words of description rather than words of limitation, the scope of the invention is indicated by the appended claims(s) rather than by the foregoing description, and all changes which come within the meaning and range of equivalency of the claim(s) are therefore intended to be embraced therein.

While the foregoing detailed description has been directed to the use of heart catheters for monitoring the heart function by transmitting its waveforms, it will be appreciated that the invention is not restricted thereto and that the transmission of other mediums are also contemplated.

For example, a heart catheter may be employed for transmitting such mediums as diastolic and systolic pressure readings, taking blood samples, introducing medicaments such as antibiotics, anticoagulants, monoclonal antibodies for bioassays, and the like.

It is also visualized that the invention may be utilized with catheters other than heart catheters, e.g. for such healthcare functions as IV therapy, parenteral feeding and the like.

Since certain changes may be made without departing from the scope of the invention herein contemplated, it is intended that all matter in the foregoing specification and drawings shall be taken as illustrative and not in a limiting sense.

The invention claimed is:

1. An adapter kit for a catheter introducer for a catheter, comprising:
   a body member having a cavity;
   an elastomeric means in said cavity;
   a compression member aligned with said cavity, said compression member having a tubular plunger aligned with said cavity;
   said body member having a mouth in said cavity for receiving said tubular plunger, said mouth having a bore lip having an internal dimension less than the internal dimensions of said cavity;
   said elastomeric means being two silicone elastomeric glands with approximately a 40 Shore A (durometer hardness), each of different length, having approximately the same outside dimension for fitting interchangeably in said cavity, so that the glands can be used interchangeably, each with a different outside dimensioned catheter gripped by the compression of a different length gland;
   said elastomeric glands each being cut in a different length from the same extrusion and having a bore of approximately the same cross sectional dimensions, said elastomeric gland being telescoped over the catheter;
   said elastomeric glands having outside diameters greater than the internal dimension of said bore lip and fitting into the internal dimension of said cavity, so that said glands can be telescoped through said mouth into said cavity and detachably held in said cavity by said bore lip; and
   a coupling means responsive to bringing together and connecting said members for compressing said elastomeric means against the catheter by said compression member in a controlled manner in a catheter gripping position, said gripping position being the same in use with either elastomeric gland so that the catheter is not adversely crushed.

2. The adapter kit of claim 1, wherein said coupling means includes an adjusting means for adjusting the relative positions of said body and compression members, said adjusting means having cooperating threads on said body and compression members.

3. The adapter kit of claim 2, wherein said catheter gripping position is determined by abutting stops including stop shoulders on said body and compression members.

4. The adapter kit of claim 3, wherein said abutting stops further comprise said cooperating threads ending in thread run out.

5. An adapter kit for a catheter introducer for a catheter, the catheter having a specific outside dimension and at least one lumen containing a medium for transmitting a waveform, the waveform being responsive to a compression of the catheter, said adapter kit comprising;
   a body member having a cavity;
   an elastomeric means within said cavity, said elastomeric means being an elastomeric gland having a preselected length for use with the specific outside diameter of the catheter, said gland having above and being telescoped over the catheter, the elastomeric gland comprising a plurality of interchangable annular cylindrical elastomeric glands cut from the same extrusion, each having the same inside diameter and the same outside diameter, said glands having different lengths, each for use with a different size catheter having a different outside diameter;

a compression member aligned with said cavity, said compression member having a plunger aligned with said cavity;

a coupling means for bringing together said body member and said compression member into a catheter gripping position, said gripping position being the same in use with each elastomeric gland, resulting in the compression of said bore of said gland and the outside diameter of the catheter, so that the catheter is gripped by said gland without distorting the transmitted waveform.

6. The adapter kit of claim 5, wherein said coupling means includes an adjusting means for adjusting the relative positions of said body and compression members, said adjusting means having cooperating threads on said body and compression members.

7. The adapter kit of claim 6, wherein said catheter gripping position is determined by abutting stops including stop shoulders on said body and compression members.

8. The adapter kit of claim 7, wherein said abutting stops further comprise said cooperating threads ending in thread run out.

9. The adapter kit of claim 5, wherein said elastomeric gland is a silicone gland having a 40 Shore A (durometer hardness).

10. The adapter kit of claim 5, wherein said cavity of said body member has a mouth for receiving said plunger, said mouth having a bore lip having an internal dimension less than the internal dimensions of said cavity, said gland having an outside dimension greater than said internal dimension of said bore lip and fitting into the internal dimension of said cavity, so that said gland can be telescoped through said mouth into said cavity and detachably held in said cavity by said bore lip.

11. The adapter kit of claim 10, wherein said cavity and said bore lip are coaxial and annular in shape, said plunger is a tubular plunger having an outer lip having an outer dimension slightly greater than the internal dimension of said bore lip, so that said outer lip of said plunger moves past said bore lip in a snap action and detachably connects said body and compression members in a free spin position, so that either said body or compression member can rotate coaxially without cocking or binding.

* * * * *